(12) United States Patent
Lechot et al.

(10) Patent No.: US 7,296,804 B2
(45) Date of Patent: Nov. 20, 2007

(54) HAND-HELD INSTRUMENT HOLDER FOR SURGICAL USE

(75) Inventors: André Lechot, Orvin (CH); Philippe Fehlbaum, Lignières (CH)

(73) Assignee: Precimed S.A., Orvin (CH)

( * ) Notice: Subject to any disclaimer, the term of this patent is extended or adjusted under 35 U.S.C. 154(b) by 89 days.

(21) Appl. No.: 10/429,897

(22) Filed: May 5, 2003

(65) Prior Publication Data

US 2004/0220554 A1    Nov. 4, 2004

Related U.S. Application Data

(63) Continuation-in-part of application No. 10/391,464, filed on Mar. 18, 2003, now Pat. No. 7,056,317, which is a continuation of application No. 09/902,369, filed on Jul. 9, 2001, now Pat. No. 6,540,739, which is a continuation of application No. 09/602,341, filed on Jun. 24, 2000, now Pat. No. 6,264,647.

(51) Int. Cl.
*B23B 31/107* (2006.01)

(52) U.S. Cl. ............................ 279/75; 279/71; 279/81; 279/140; 279/155; 408/226; 408/240; 606/62; 606/67; 606/99; 606/104

(58) Field of Classification Search ................. 279/71, 279/74, 75, 81, 82, 140, 155; 408/226, 240; 606/62, 67, 99, 104; 81/489, 491
See application file for complete search history.

(56) References Cited

U.S. PATENT DOCUMENTS

| | | | | |
|---|---|---|---|---|
| 3,583,715 A | * | 6/1971 | Jahrl ............................ 279/75 |
| 4,661,009 A | * | 4/1987 | Tripp ........................... 403/349 |
| 4,692,073 A | * | 9/1987 | Martindell .............. 408/239 A |
| 4,768,405 A | * | 9/1988 | Nickipuck ............... 81/177.85 |
| 4,858,939 A | * | 8/1989 | Riggs ........................... 279/75 |
| 5,062,749 A | * | 11/1991 | Sheets .......................... 279/75 |
| 5,190,422 A | * | 3/1993 | Lechot ................... 408/239 R |
| 5,222,848 A | * | 6/1993 | Kuang-Wu .............. 408/239 R |
| 5,236,433 A | * | 8/1993 | Salyer .......................... 606/91 |
| 5,271,697 A | * | 12/1993 | Johnson et al. ............. 408/222 |
| 5,407,293 A | * | 4/1995 | Crainich ................... 403/322.1 |
| 5,464,300 A | * | 11/1995 | Crainich ................... 403/322.1 |

(Continued)

FOREIGN PATENT DOCUMENTS

DE    39 34 610 A1    4/1991

(Continued)

*Primary Examiner*—Monica Carter
*Assistant Examiner*—Michael W. Talbot
(74) *Attorney, Agent, or Firm*—Moetteli & Associés SàRL (57) ABSTRACT

A surgical instrument holder has a shank having a coupling end, a handle attached to an opposite end of the shank, a coupling device, and a locking mechanism. The coupling end has an interface thereon for receiving an instrument. The locking mechanism has an annular locking component, a spring, a ring which slides on the shank, and a locking device. The annular locking component is mounted so as to slide along the shank. The locking device cooperates with the locking component so as to lock the instrument onto the interface. The spring biases the locking component in a locking direction and bears on the ring. The ring is disengageably lockable to the shank via a connection device so as to enable quick disassembly for cleaning and component sterilization.

31 Claims, 7 Drawing Sheets

U.S. PATENT DOCUMENTS

| | | | |
|---|---|---|---|
| 5,569,256 A * | 10/1996 | Vaughn et al. | 606/80 |
| 5,586,847 A * | 12/1996 | Mattern et al. | 408/239 A |
| 5,658,290 A * | 8/1997 | Lechot | 606/80 |
| 5,817,096 A * | 10/1998 | Salyer | 606/81 |
| 5,988,957 A * | 11/1999 | Wheeler | 408/239 R |
| 6,129,392 A | 10/2000 | Sauer | |
| 6,179,302 B1 * | 1/2001 | Gauthier et al. | 279/75 |
| 6,264,647 B1 | 7/2001 | Lechot | |
| 6,457,916 B2 * | 10/2002 | Wienhold | 408/240 |
| 6,475,221 B1 * | 11/2002 | White et al. | 606/80 |
| 6,506,000 B2 * | 1/2003 | Lechot | 407/35 |
| 6,540,739 B2 * | 4/2003 | Lechot | 606/1 |
| 6,666,114 B1 * | 12/2003 | Lin | 81/438 |
| 6,669,702 B2 * | 12/2003 | Lechot | 606/86 |
| 6,722,667 B2 * | 4/2004 | Cantlon | 279/22 |
| 6,875,217 B2 * | 4/2005 | Wolford | 606/81 |
| 2003/0004530 A1 | 1/2003 | Reo | |
| 2003/0178797 A1 * | 9/2003 | Lovchik et al. | 279/75 |
| 2003/0216716 A1 * | 11/2003 | Desarzens | 606/1 |
| 2004/0102763 A1 * | 5/2004 | Lechot | 606/1 |
| 2005/0015097 A1 * | 1/2005 | Mujwid et al. | 606/104 |

FOREIGN PATENT DOCUMENTS

| | | |
|---|---|---|
| WO | WO 2004096069 A1 * | 11/2004 |
| WO | WO 2004098421 A1 * | 11/2004 |

* cited by examiner

HAND-HELD INSTRUMENT HOLDER FOR SURGICAL USE

CROSS REFERENCE TO RELATED APPLICATIONS

This application is a continuation-in-part of U.S. patent application Ser. No. 10/391,464, entitled instrument Holder for a Surgical instrument, filed on Mar. 18, 2003 and now U.S. Pat. No. 7,056,317, which is in turn continuation of Ser. No. 09/902,369 filed on Jul. 9, 2001, U.S. Pat. No. 6,540,739 which in turn is a continuation of Ser. No. 09/602,341 filed Jun. 24, 2000 and now U.S. Pat. No. 6,264,647 issued Jul. 24, 2001, the contents of which are incorporated herein by reference thereto.

BACKGROUND OF THE INVENTION

This invention relates to surgical instrument holders, and more particularly, to hand-held holders of rotary surgical cutting tools.

Surgical instruments and their respective holders have to be kept clean and sterile before any use in a hospital environment in order to minimize risk of transfer of disease or infection from patient to patient following the emergence of certain "prions" that are not killed by normal hospital sterilization and thus need to be physically removed through washing and rinsing. A surgical instrument, for example for preparing for the fitting of a hip prosthesis, works in a medium which causes considerable soiling of the instrument and of the instrument holder. Despite the importance of doing so, the thorough cleaning of these devices is difficult. Surgical instrument holders of the prior art are designed such that washing and rinsing are generally not an effective way of cleaning the instrument. This is due to the small spaces left between component parts which allow only minimal access by cleaning agents.

What is needed therefore is a surgical instrument holder which is quickly and simply disassembled for cleaning and sterilization.

SUMMARY OF THE INVENTION

The surgical instrument holder of the invention has a shank having first driveable end and second coupling end, a coupling device mounted on the coupling end, and a locking mechanism. The coupling end has an interface thereon for receiving an instrument. The locking mechanism in made up of an annular locking component, a spring, a ring which slides on the shank, and a locking device. The annular locking component is mounted so as to slide along the shank. The locking device cooperates with the locking component so as to lock the instrument onto the interface. The spring biases the locking component in a locking direction and bears on the ring. The ring is disengageably lockable to the shank via a connection device.

The object of the invention is to enable quick disassembly for cleaning and component sterilization.

In a feature of the invention, the holder is adapted to hold a large AO fitting.

In another feature of the invention, the holder is adapted to hold a small AO fitting.

BRIEF DESCRIPTION OF THE DRAWINGS

The attached drawings show embodiments of the invention by way of example.

DETAILED DESCRIPTION OF THE PREFERRED EMBODIMENT(S)

Figure 1:
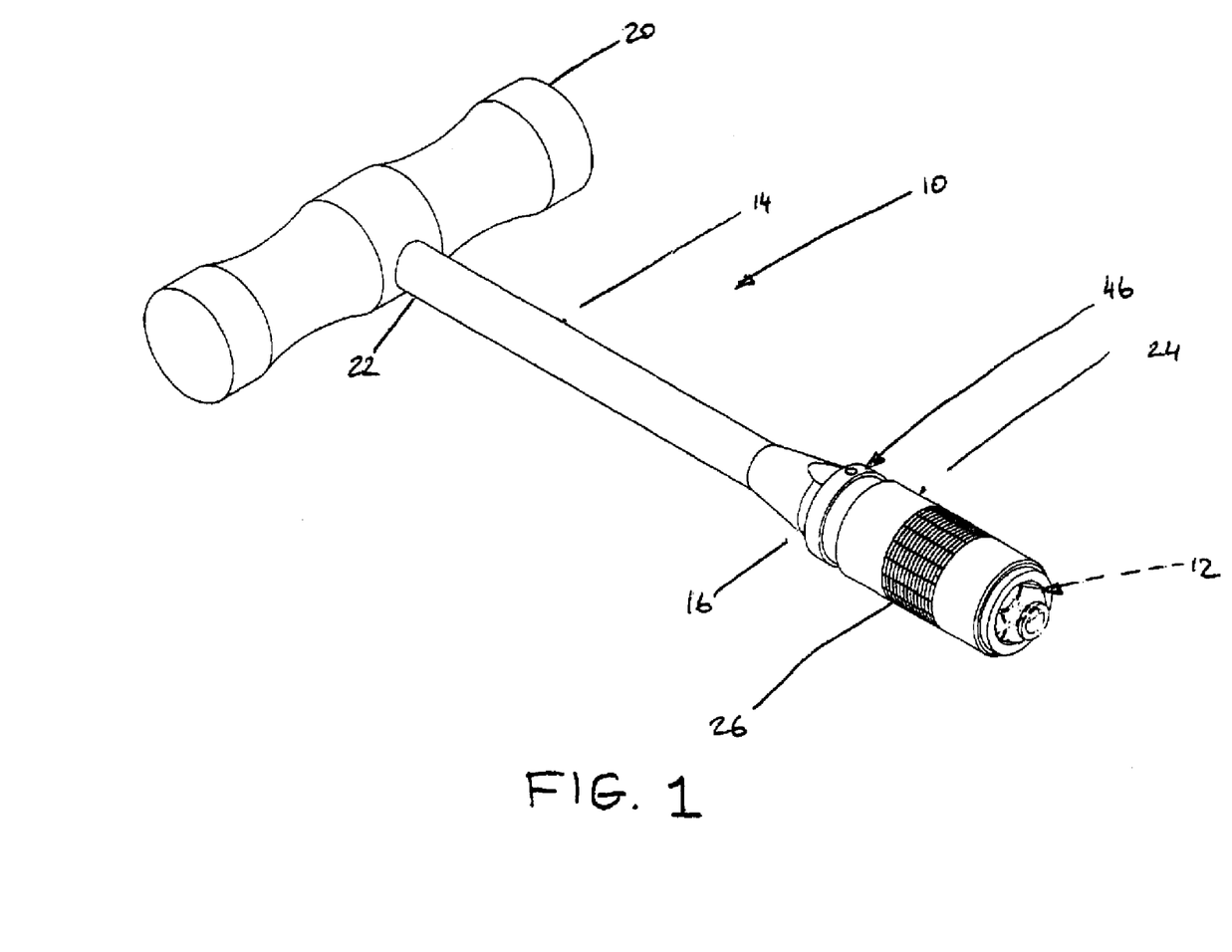
FIG. 1 is a perspective view of a first embodiment of the instrument holder of the invention, in a locked position.
Figure 2:
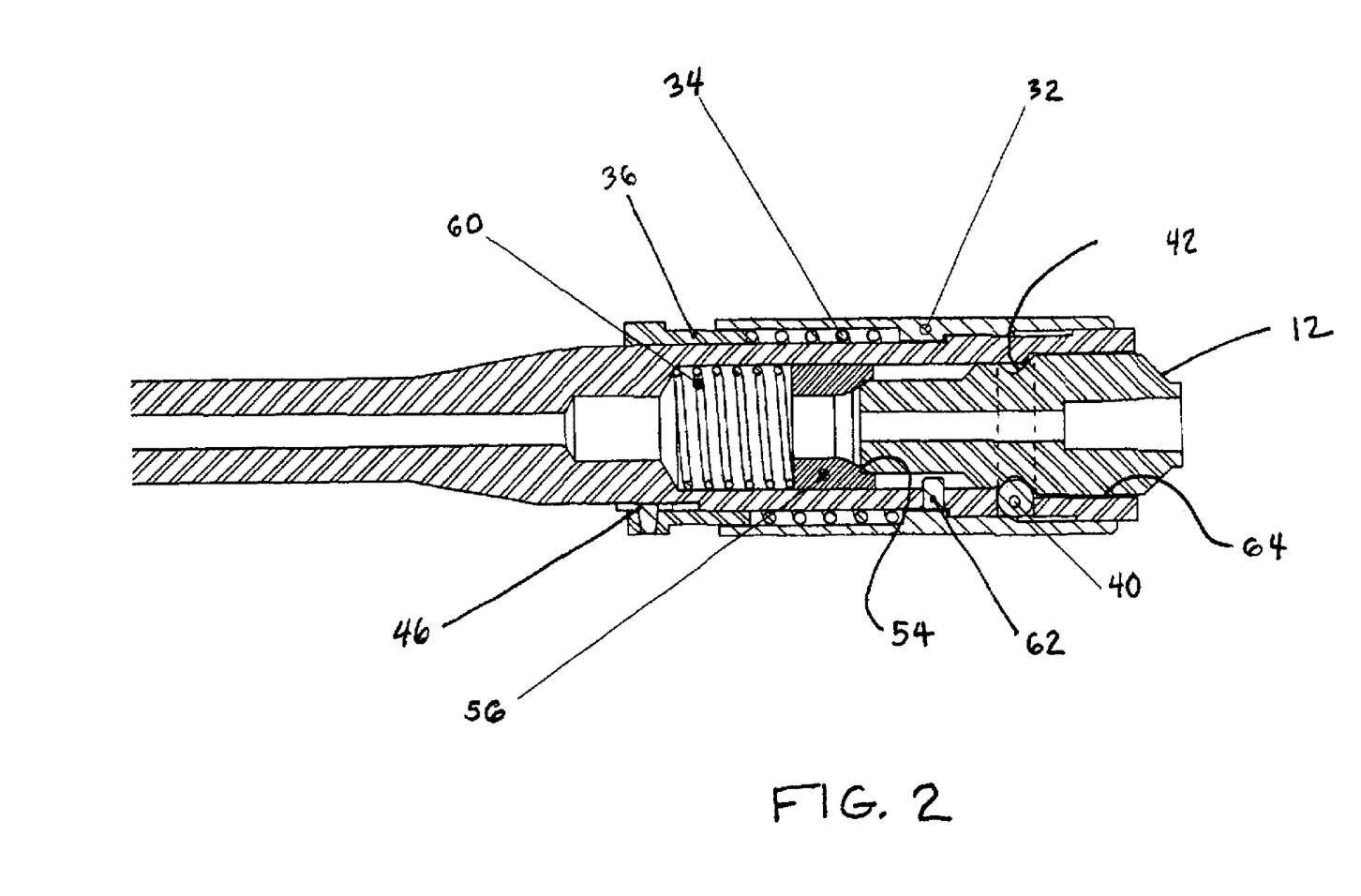
FIG. 2 is a longitudinal cross section of the instrument holder of FIG. 1.

Referring now to FIGS. 1 and 2, in which a first embodiment of the surgical instrument holder 10 of the invention is shown, the holder connects to a surgical instrument 12 to enable controlled manipulation of that instrument. The holder 10 has a shank 14 having a coupling end 16, a T-bar handle 20 attached to an opposite end 22 of the shank, a coupling device 24, and a locking mechanism 26. The coupling end 16 has an internal recess 30 therein, co-axial with the central axis of the shank, for receiving the instrument 12. The locking mechanism 26 is made up of an annular locking sleeve 32, a helical compression spring 34, a ring 36 which slides on the shank 14, and ball-detents 40. Preferably, to ensure that the instrument 12 is retained in an axially aligned relationship with the holder 10, three, circumferentially spaced apart ball-detents 40 arc disposed in the coupling end 16 of the shank 14. It should be noted that the balls 44 are held in their respective detents via any known means of doing so, such as by deforming of an edge of the detent so as to prevent the ball from being able to drop out or by use of a ball-detent pre-assembly that threads in a threaded hole.

The annular locking sleeve 32 mounts so as to slide along tile shank 14. The ball-detent 40 is disposed in the coupling end 16 of the shank 14 and received into an annular recess 42 in the instrument. The locking sleeve 32 slides over the ball-detent 40 to bias balls 44 into the recess 42 in order to minimize play in the connection. The spring 34 biases the locking sleeve 32 in a locking direction and bears on the ring 36. The ring 36 is disengageably lockable to the coupling end 16 of the shank 14 via a catch such as a bayonet mechanism 46. The bayonet mechanism 46 includes a bayonet slot 50 and a locking pin 52. The bayonet slot 50 is cut in the coupling end 16 of the shank 14.

The ring 36 locks over the coupling end 16, and the shank 14 has a smaller diameter than the coupling end, so that when the ring is unlocked and slid back along the shank, cleaning access to all surfaces of the locking mechanism 26 is facilitated.

Optionally, the shank is hollow along its length so as to provide a channel facilitating chip removal.

Referring in particular to FIG. 2, a chamfered surface 54 is disposed within the recess 30 to align the instrument axially. The chamfered surface 54 is disposed on an annular piston 56. The piston 56 is free to slide within the recess, biased toward the instrument by an internal spring 60. A locking element 62 prevents the piston 56 from exiting the recess 30. The piston 56 contacts the instrument 12 as the instrument enters the recess 30 prior to and as the instrument is aligned with the ball-detent 40, so as to enable locking of the instrument in an axially aligned configuration.

The recess 30 includes a hexagonal female portion 64 for engaging a corresponding surface of the instrument. The ball-detents 40 are located in the coupling end 16 of the shank 14 adjacent the hexagonal female portion 64.

The holder 10 of the first embodiment is adapted to a large AO fitting 12.

Figure 3:
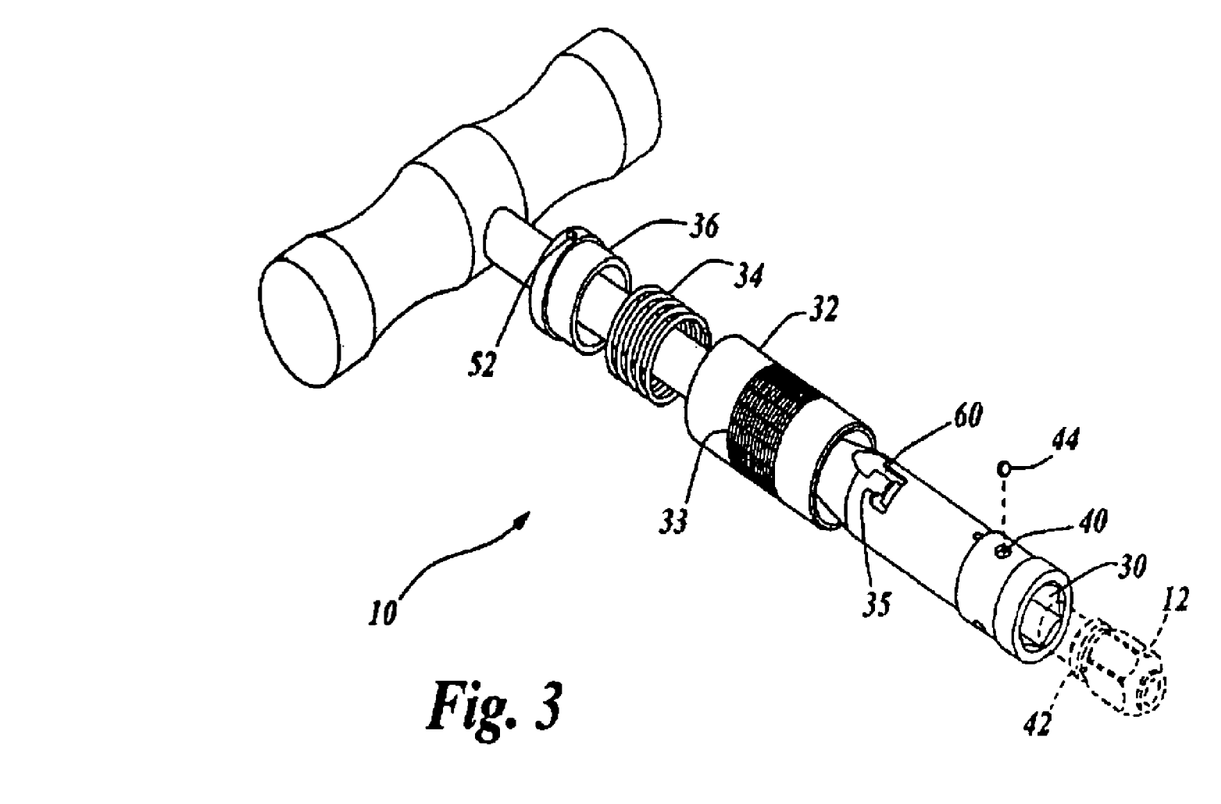
FIG. 3 is a perspective view of the instrument holder, in an unlocked position, ready for cleaning.

Referring now to FIG. 3, the instrument holder 10 is shown in an unlocked, partially disassembled position, ready for cleaning. To unlock the holder 10, the ring 36 is urged against the bias of spring 34 so as to be lifted out of a bayonet seat 35, and then twisted so as to move the pin 52 out of the bayonet slot 50 in the coupling end 16 of the shank 14. The ring 36 may then be slid back along the shank 14, releasing the spring 34 and the sleeve 32, and thereby providing cleaning and sterilization access to the recesses that might otherwise not be accessible. The instrument 12 is shown in dashed lines, as it is not part of the invention 10. A knurled surface 33 is apparent on the sleeve 32. Such surface 33 improves the grip of the user on the sleeve 32 when the user pulls back on the sleeve to release the instrument 12.

Figure 4:
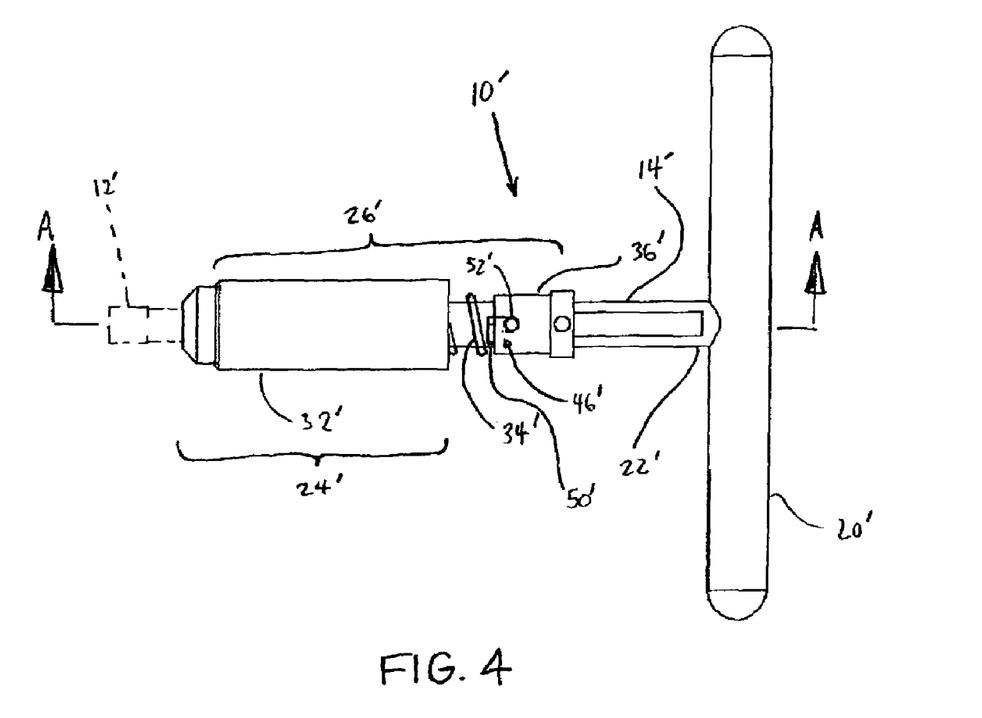
FIG. 4 is a top plan view of a second embodiment of the instrument holder of the invention, in a locked position.
Figure 5:
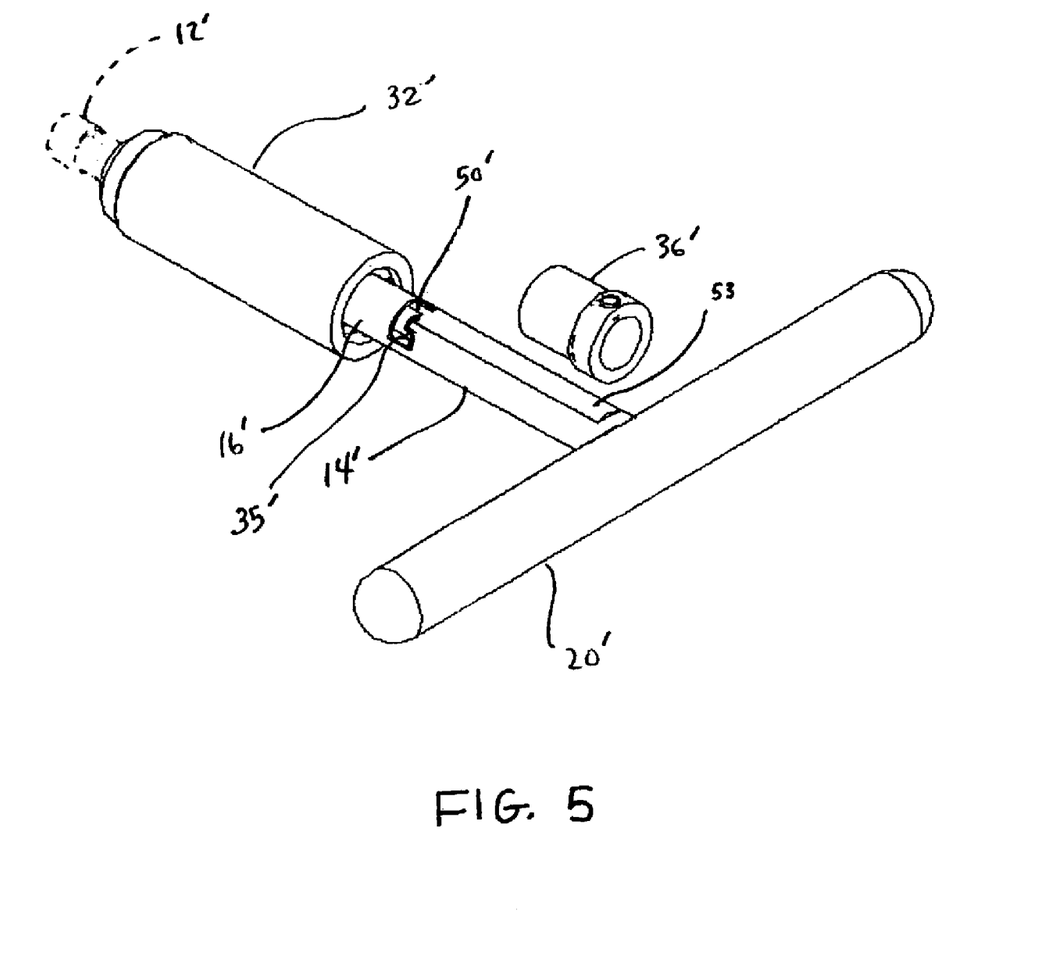
FIG. 5 is a perspective view of the second embodiment, exposing a bayonet slot.

Referring now to FIG. 4, in which is shown a second embodiment of the instrument holder 10' of the invention, the holder has a shank 14' having a coupling end 16', a T-bar handle 20' attached to an opposite end 22' of the shank, a coupling device 24', and a locking mechanism 26. The coupling end 16' has an internal recess 30' therein, co-axial with the central axis of the shank, for receiving an instrument 12', which is a small AO fitting (shown most clearly in FIG. 7). The locking mechanism 26' is made up of an annular locking sleeve 32', a helical spring 34', a ring 36' which slides on the shank 14', and a ball-detent 40'. The annular locking sleeve 32' mounts so as to slide along the shank 14'. The ball-detent 40' is disposed in the coupling end 16' of the shank 14' and received into an annular recess 42' in the instrument 12'. The locking sleeve 32' slides over the ball-detent 40' to bias the ball 44' into the recess 42' in order to lock the instrument 12' in place as well as to minimize play in the connection. The spring 34' biases the locking sleeve 32' in a locking direction and bears against the ring 36'. The ring 36' is disengageably lockable to the coupling end 16' of the shank 14' via a bayonet mechanism 46'. The bayonet mechanism 46' includes a bayonet slot 50' (best shown in FIG. 5) and a locking pin 52'. The bayonet slot 50' is cut in the coupling end 16' of the shank 14', and includes a seat 35'. Note that in this embodiment, the internal diameter of the ring 36' is only just larger than the external diameter of the shank 14' in its mid portion, and that a flat 53 provides clearance for the pin 52', so that it is able to slide out of the bayonet slot 50' and then along the shank.

Figure 6:
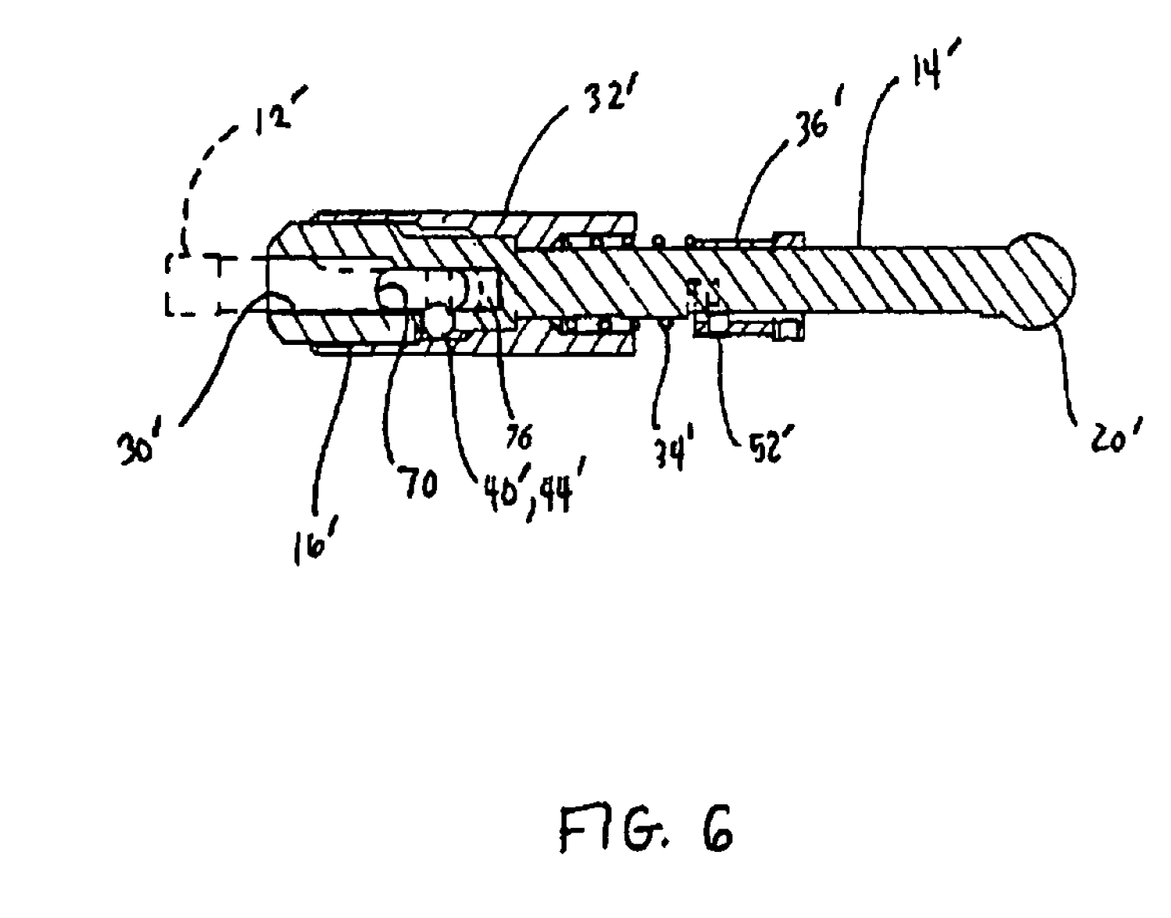
FIG. 6 is a cross sectional view taken along line A-A of FIG. 4, in a locked position.

Referring now to FIG. 6, showing the holder 10' in a locked position, locking the instrument 12', the coupling end 16' includes a transverse slot 70 which penetrates into the recess 30', axially offset therefrom so as to create an offset wall 72 which engages a corresponding flat surface 74 of an instrument 12'. At the end of the recess 30', a D-shaped seat 76 interfaces with the instrument 12' about its entire circumference is provided. Essentially, the seat 76 is a D-shaped blind hole shaped to closely interface with the circumference of the instrument 12'. It should be noted that this seat 76 is either cut with a carbon electrode in an EDM process or is broached in a subcomponent of the shank and then welded to a shank body to create the shank 14'. The ball-detent 40' enters an annular groove 66' in the instrument 12' along an axis perpendicular to the flat surface 74 of the instrument. A locking sleeve 32' slides over the ball detent 40' to bias a ball 44' into the recess 30' in order to lock the instrument 12' in place and to minimize play in the connection.

Figure 7:
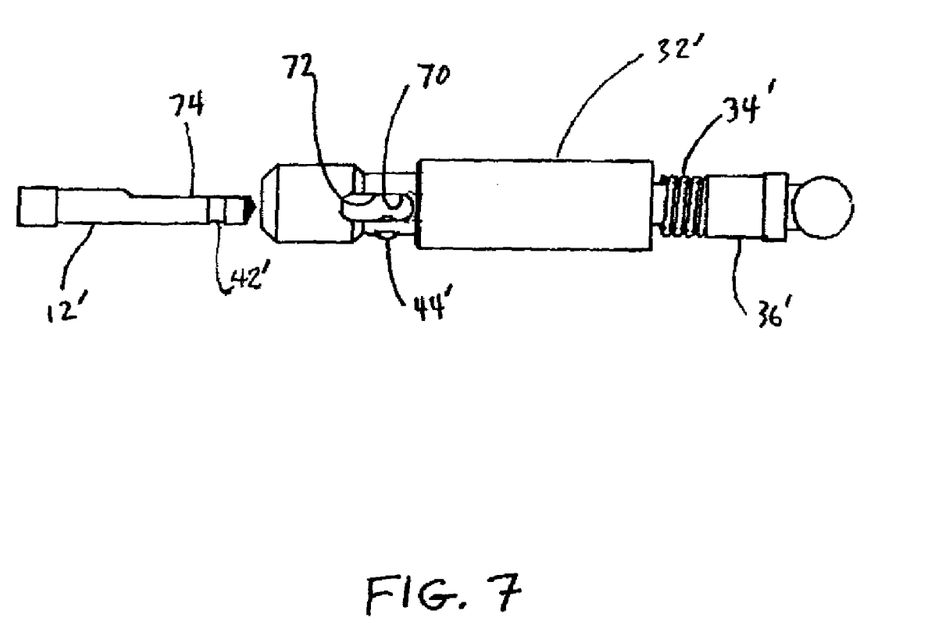
FIG. 7 is a side view of the second embodiment of the invention, in an unlocked position, ready for cleaning.

Referring now to FIG. 7, a side view of the holder 10' is shown, in an unlocked position, ready for cleaning. Note that the slot 70 not only provides the wall which locks the instrument 12' against rotation, but also provides better access for cleaning of the coupling end 16' of the holder 10'.

In an advantage of the invention, the bayonet mechanism 46 or 46' holding the ring 36' and thus the spring 34', in an operational position, enables quick disassembly for cleaning and component sterilization.

In another advantage of the invention, the large differences in diameter between the ring 36 and the shank 14 permits better access to otherwise inaccessible recesses for more thorough cleaning.

In another advantage of the invention, the holder is adapted to hold many different instrument interfaces.

In another advantage, the holder 10, 10' of the invention minimizes play and maximizes alignment with the turning axis.

Although illustrative embodiments of the invention have been shown and described a wide range of modification, change and substitution is contemplated in the foregoing disclosure and in some instances, some features of the present invention may be employed without a corresponding use of the other features. Further, the small and large AO fittings 12 and 12' are only examples of the types of instruments that the invention may be adapted to hold. In fact, there are many different varieties of fittings to which the invention is easily adaptable. For example, the invention may be adapted to hold a "ZIMMER-HALL" ("STRYKER"), a "ZIMMER", "HARRIS", "HUDSON", "TRIPAN", "JACOBS", and "QUEUES", to name a few. The elastic devices used of course can be selected from a large variety of equivalents to a helical, compression spring, including, for example, leaf springs, flat springs, multiple compression springs, just to name a few. Further, the ball-detent can be substituted with any sort of mechanical retention system, for example, a moving finger or a twisting cam shaft, etc. Still further, the connection mechanism can be substituted for a variety of connection mechanisms such as a threaded connection mechanism, a clasp, spring detents, or even magnetic retention devices. Accordingly it is appropriate that the appended claims be construed broadly and in a manner consistent with the scope of the invention.

What is claimed is:

1. A surgical instrument holder comprising a shank having first driveable end and second coupling end, the second end a having an interface for receiving a surgical instrument, wherein the interface is a recess in the coupling end of the shank with the recess being coaxial with a central axis of the shank and having a polygonal cross section which rotationally aligns the surgical instrument, the coupling device held in functional assembly to the shank by a releasable locking mechanism comprised of a ring having a catch, the ring being slideably disposed about the shank, a spring biased in a locking direction against the coupling device by the ring, and the catch disengageably retaining the ring in a fixed position during use, wherein the ring locks over the shank, and whereupon release of the catch enables quick disassembly for cleaning and component sterilization, the catch being engaged in such a way that the release of the locking ring allows for partial disassembly for cleaning while retaining all the components of the holder together.

2. The surgical instrument holder of claim 1, wherein the interface has a locking device for locking the instrument onto the interface.

3. The surgical instrument holder of claim 2, wherein the locking device is disposed in the coupling end of the shank.

4. The surgical instrument holder of claim 2, wherein the locking device comprises at least one ball-detent.

5. The surgical instrument holder of claim 4, wherein the locking device comprises at least three circumferentially spaced apart ball-detents.

6. The surgical instrument holder of claim 4, wherein the interface is a recess including a hexagonal female portion for engaging a corresponding surface of the instrument.

7. The surgical instrument holder of claim 6, wherein the ball-detent is adjacent the hexagonal female portion.

8. The surgical instrument holder of claim 7, wherein the ball-detent is received into an annular recess in the instrument, the locking device sliding over the ball detent to bias a ball into the recess to minimize play in the connection.

9. The surgical instrument holder of claim 8, wherein the holder is adapted to hold a large AO fitting.

10. The surgical instrument holder of claim 2, wherein the surface corresponding to the surface of the surgical instrument is an inner surface of an annular piston, which piston slides within the recess and is biased toward the instrument by an elastic device, the piston contacting the instrument as the instrument enters the recess and is aligned with the inner surface, and wherein a locking element prevents the annular piston from exiting the recess, the locking element being a pin for engaging a bayonet slot on the instrument so as to enable locking of the instrument in an axially aligned configuration.

11. The surgical instrument holder of claim 1, wherein the coupling device comprises a coupling sleeve against which the spring is biased by the ring, the sleeve being slideable about the shank so as to operate a ball-detent mechanism wherein a ball is held so as to prevent the ball from being able to drop out of the mechanism when the holder is partially disassembled for cleaning.

12. The surgical instrument holder of claim 11, wherein a chamfered surface aligns the instrument axially, the chamfered the surface disposed on an annular piston which slides within the recess, the annular piston biased toward the instrument by an elastic device, wherein further, a locking element prevents the annular piston from exiting the recess, the piston contacting the instrument as the instrument enters the recess prior to and as the instrument is aligned with the ball-detent, so as to enable locking of the instrument in an axially aligned configuration.

13. The surgical instrument holder of claim 1, wherein a handle is attached to the first end of the shank.

14. The surgical instrument holder of claim 1, wherein the spring is a helical compression spring.

15. The surgical instrument holder of claim 1, wherein the locking direction is toward the coupling end of the shank.

16. The surgical instrument holder of claim 1, wherein the catch is a bayonet mechanism.

17. The surgical instrument holder of claim 16, wherein the bayonet mechanism is comprised of a bayonet slot and a locking pin.

18. The surgical instrument holder of claim 17, wherein the bayonet slot is disposed on the shank.

19. The surgical instrument holder of claim 1, wherein the interface is a recess intersected by a transverse slot wherein a wall of the slot engages a corresponding flat surface of the instrument.

20. The surgical instrument holder of claim 19, wherein the recess includes a seat shaped to receive the end of the instrument about its entire circumference.

21. The surgical instrument holder of claim 20, wherein a ball-detent enters an annular groove in the instrument along an axis perpendicular to the flat surface of the instrument.

22. The surgical instrument holder of claim 21, wherein the locking device slides over the ball detent to bias a ball into the recess in order to minimize play in the connection.

23. The surgical instrument holder of claim 1, wherein the holder is adapted to hold a small AO fitting.

24. The surgical instrument holder of claim 1, wherein the shank is hollow along its length so as to provide a channel facilitating chip removal.

25. The surgical instrument holder of claim 1, wherein a T-bar handle is attached to the first end of the shank.

26. The surgical instrument holder of claim 1, wherein the polygonal surface being a hexagonal surface.

27. The surgical instrument holder of claim 1, wherein the polygonal surface comprises a flat surface.

28. The surgical instrument holder of claim 1, wherein the shank has a smaller diameter than the coupling end.

29. A surgical instrument holder providing a connection to a surgical instrument, comprising a shank, the shank having first driveable end and second coupling end, a T-bar handle attached to the first end of the shank, a coupling device, and a locking mechanism, wherein the coupling end has an internal recess therein for receiving an instrument, wherein the locking mechanism comprises an annular locking sleeve, a helical spring, a ring which slides on the shank, and a ball-detent mechanism wherein the ball is held so as to prevent the ball from being able to drop out of the mechanism and, the annular locking sleeve mounted so as to slide along the shank, the ball-detent being disposed in the coupling end of the shank and received into an annular recess in the instrument, the locking sleeve sliding over the ball detent to bias a ball into the recess to minimize play in the connection, wherein the spring biases the locking sleeve in a locking direction and bears on the ring, the ring being disengageably lockable to the coupling end of the shank via a bayonet mechanism comprised of a bayonet slot and a locking pin so as to enable quick disassmbly for cleaning and componet sterilization, wherein release of the ring allows for partial dissembly for cleaning while retaining all the componets of the holder together.

30. A surgical instrument holder comprising:
a shank having first driveable end and second coupling end;
a "T"-handle disposed at the first driveable end;
a coupling device disposed at the second end, the coupling device held in functional assembly to the shank by a releasable locking mechanism and having an interface for receiving a surgical instrument; and
the releasable locking mechanism comprising a ring slideably disposed about the shank, a spring biased against the coupling device by the ring, and a bayonet mechanism comprised of a bayonet slot and a locking pin, the bayonet slot disposed on the shank, the bayonet mechanism retaining the ring in a fixed position during use, whereupon release of the bayonet mechanism enables quick disassembly of the ring, spring and coupling device for cleaning and component sterilization, wherein release of the ring allows for partial disassembly for cleaning while retaining all the components of the holder together.

31. A surgical instrument holder comprising a shank having first driveable end and second coupling end, the second end comprising a coupling device operating a ball-detent mechanism wherein the ball is held so as to prevent the ball from being able to drop out of the mechanism, and having an interface for receiving a surgical instrument, wherein the interface is a recess in the coupling end of the shank with the recess being coaxial with a central axis of the shank and having a polygonal cross section which rotationally aligns the surgical instrument and corresponds to a cross section of the surgical instrument, the corresponding cross section selected from the group consisting of a hexagonal cross section and a cylindrical cross section having a flat, and the coupling device held in functional assembly to the shank by a releasable locking mechanism comprised of a ring having a catch, the ring being slideably disposed about the shank, a spring biased in a locking direction against the coupling device by the ring, and the catch disengageably retaining the ring in a fixed position during use, wherein the ring locks over the shank, and the shank has a smaller diameter than the coupling end, and whereupon release of the catch enables quick disassembly for cleaning and component sterilization, the catch being engaged in such a way that the release of the locking ring allows for partial disassembly for cleaning while retaining all the components of the holder together.

* * * * *

UNITED STATES PATENT AND TRADEMARK OFFICE
CERTIFICATE OF CORRECTION

PATENT NO.       : 7,296,804 B2
APPLICATION NO.  : 10/429897
DATED            : November 20, 2007
INVENTOR(S)      : André Lechot and Philippe Fehlbaum It is certified that error appears in the above-identified patent and that said Letters Patent is hereby corrected as shown below:

In Col. 2, line 33, replace the phrase "arc disposed" with --are disposed--.

In Col. 2, line 41, replace the phrase "tile shank" with --the shank--.

In Col. 3, line 66, replace the phrase "an annular groove 66' in the" with --an annular groove 42' in the--.

In Col. 4, line 52, replace the phrase "a having an interface" with --having an interface--.

In Col. 6, line 42, replace the phrase "disassmbly for cleaning" with --disassembly for cleaning--.

Signed and Sealed this

Thirteenth Day of May, 2008

JON W. DUDAS
*Director of the United States Patent and Trademark Office*